United States Patent [19]

Honig et al.

[11] 3,943,200
[45] Mar. 9, 1976

[54] BIS ALKYL PHOSPHORUS ESTERS OF DICARBOXYLIC ACIDS

[75] Inventors: Milton L. Honig, New York; Edward N. Walsh, New City, both of N.Y.

[73] Assignee: Stauffer Chemical Company, Westport, Conn.

[22] Filed: July 15, 1974

[21] Appl. No.: 488,632

[52] U.S. Cl. ............................................. 260/932
[51] Int. Cl.² .......................................... C07F 9/40
[58] Field of Search .......................... 260/932, 969

[56] References Cited
UNITED STATES PATENTS

| | | | |
|---|---|---|---|
| 2,634,288 | 4/1953 | Boyer et al. | 260/932 |
| 2,957,904 | 10/1960 | Stiles | 260/932 |
| 3,012,054 | 12/1961 | Moss | 260/932 |

*Primary Examiner*—Richard L. Raymond
*Attorney, Agent, or Firm*—Richard P. Fennelly

[57] ABSTRACT

Bis alkyl phosphorus esters of dicarboxylic acids having the formula

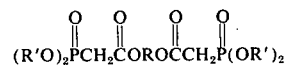

where R' is a $C_1$–$C_8$ alkyl or haloalkyl group, preferably a $C_1$–$C_4$ alkyl or haloalkyl group, and R is a $C_1$–$C_8$ divalent hydrocarbon group are disclosed. The compounds are formed by the reaction of a tertiary phosphite having the formula $P(OR')_3$ with a haloalkyl ester of a dicarboxylic acid having the formula $XCH_2C(O)ORO(O)CCH_2X$, where X is chlorine, bromine or iodine. The compounds have utility as flame retardants and as sequesterants for metallic cation.

11 Claims, No Drawings

BIS ALKYL PHOSPHORUS ESTERS OF DICARBOXYLIC ACIDS

TECHNICAL DESCRIPTION OF THE INVENTION

The invention relates to bis alkyl phosphorus esters of dicarboxylic acids having the formula

where R' is a $C_1$–$C_8$ alkyl group or haloalkyl, e.g., chlorine or bromine substituted, preferably a $C_1$–$C_4$ group, e.g., an ethyl or chloroethyl group, and R is a $C_1$–$C_8$ divalent hydrocarbon group which can be a $C_1$–$C_8$ substituted or unsubstituted alkylene group, e.g., —CH$_2$—C(CH$_2$Br)$_2$—CH$_2$—, or, as preferred, a $C_2$ alkylene group, or a divalent $C_1$–$C_8$ hydrocarbon group having arylene or ethylenic unsaturation interruption in its hydrocarbon chain, e.g., —CH$_2$—C$_6$H$_4$—CH$_2$— or —CH$_2$C(Br)=C(Br)CH$_2$—.

The above compounds are preferably formed by reacting an ester of the formula XCH$_2$CO$_2$RO$_2$CCH$_2$X, where R has the meaning given above, the X is chlorine, bromine or iodine, with a trialkyl phosphite having the formula (R'O)$_3$P. The reaction between a glycol, HOROH, and a haloacetic acid, XCH$_2$COOH, to form the ester is preferably carried out at temperatures ranging between 100°C. and 250°C. using a molar ratio of acid to glycol and ranging between 2.0 and 2.5. If desired, from about 0.1 to 10 percent by weight of a nucleophilic catalyst can be used. Examples of suitable catalysts are sodium carbonate, sodium hydroxide, stannous octoate, sodium methylate, sodium methoxide, sodium phenolate, sodium cresylate, potassium phenolate, sodium decylate and the sodium salt of tris(2-hydroxypropoxy) propane.

The reaction between the ester and the trialkylphosphite is carried out at elevated temperatures and gives an Arbuzov rearrangement. The preferred reaction temperature for this step is about 140°C. to 200°C. The molar ratio of bis ester to triethyl phosphite which is reacted in this step should be from about 1.8 to 2.0.

The compounds described herein have utility as sequestering agents, e.g., as a sequestering agent for zinc, calcium, magnesium, manganese, cobalt and antimony catalysts in the manufacture of polyester terephthalate fibers or fabrics, Encyclopedia of Chemical Technology, 2nd Ed., Vol. 6, pp 174–177 (1965). The compounds, particularly when their alkyl or alkylene substituents are halo-substituted, can also be used as flame retardants in such materials as plastics, cellulose, and wood.

The invention is illustrated by the following Examples:

EXAMPLE 1

A reactor fitted with a thermometer, mechanical stirrer, condenser and Dean-Stark trap was charged with 377 g. (4.0 mol) of chloroacetic acid, 124 g. (2.0 mol) of ethylene glycol, 30 g. of V,M and P Naptha and 2.0 g. stannous octoate. These were placed under a nitrogen atmosphere and slowly heated over several hours to 194°C. Water was continuously removed by distillation throughout the heat-up and totaled 69 g. Vacuum distillation of the pot afforded 335 g. of a liquid (78% yield) boiling at 105°C/0.1mm. An n.m.r. (nuclear magnetic resonance) spectrum of the product in CCl$_4$ exhibited a pair of equally intense singlets at $\tau$5.85 and $\tau$5.57, fully consistent with the bis ester.

To a flask containing a thermometer, condenser, mechanical stirrer and side-arm dropping funnel was added 107.5 g. (0.5 mol) of the bis ester. The ester was placed under nitrogen and heated to 150°C. To this was slowly added 166 g. (1.0 mol) of triethyl phosphite over a 3 hour period. Ethyl chloride was continuously evolved throughout the reaction. The 150°C temperature was maintained another 5 hours followed by 4 hours at 170°–175°C. Volatiles were then removed in a vacuum distillation. The desired product remained behind in the reactor as a yellow liquid weighing 158 g. (76% yield). An infrared spectrum of this material exhibited bands at 1740cm$^{-1}$ (C=O) and 1260cm$^{-1}$ (P=O). The n.m.r. spectrum in CCl$_4$ consisted of signals at $\tau$8.80 (12H, triplet, J=7Hz., CH$_3$CH$_2$), $\tau$6.98 (4H, doublet, J=21 Hz. PCH$_2$) and $\tau$ 6.2–5.5 (12H, multiplet, OCH$_2$).

EXAMPLE 2

An esterification reactor fitted with a Dean-Stark trap was charged with 104 g. (1.1 mol) of chloroacetic acid, 123 g. (0.5 mol) of 1,4-dibromo-2-butenediol, 1 g. of stannous octoate and 90 ml of naphtha. The reactants were heated under nitrogen at 145°–153°C. After 14 hours, 17 g. of water condensate had collected in the trap (theoretical = 18 g.). The product was diluted in 300 ml. of methylene chloride and was washed successively with water, aqueous sodium carbonate and then water. The organic layer was separated, was dried over magnesium sulfate and was solvent stripped on a rotary evaporator in vacuo. A white solid weighing 172.6 g. (0.87 mol) was obtained and represented an 87 percent yield. The crystalline product melted at 73°–74°C. An infrared spectrum indicated absence of —OH groups but showed the presence of bands at 3030 and 3010 cm$^{-1}$ (C=C) and 1765 cm$^{-1}$ (C=O).

To a refluxing solution of 60 g. (0.14 mol) of the above bis-chloroacetate in 100 g. of O-dichlorobenzene was added 99.6 g. (0.60 mol) of triethyl phosphite. Addition of phosphite was completed within 10 hours, and heating at 155°–175°C. was terminated after another three hours. The solvent was subsequently removed by vacuum distillation. A total of 78.7 g. of product remained. The infrared spectrum exhibited a carbonyl band at 1740 cm$^{-1}$.

EXAMPLE 3

The same procedure used in Example 1 is used with the exception that one mole of tris(2-chloroethyl)-phosphite is used in place of the triethyl phosphite. Ethylene dichloride, rather than ethyl chloride, is evolved. The product contains 2-chloroethyl substitution for R'.

The appended claims give the scope of protection sought.

What is claimed:

1. Compounds having the formula

wherein R' is a $C_1$–$C_8$ alkyl or haloalkyl group and R is selected from the group consisting of an unsubstituted or bromo-substituted $C_1$-$C_8$ alkylene group and an unsubstituted or bromo-substituted $C_1$-$C_8$ hydrocarbon chain group having arylene or ethylenic unsaturation interruption in its chain.

2. Compounds as claimed in claim 1 wherein R' is a $C_1$-$C_4$ alkyl group.

3. Compounds as claimed in claim 1 wherein R' is an ethyl group.

4. Compounds as claimed in claim 1 wherein R' is 2-chloroethyl.

5. Compounds as claimed in claim 1 wherein R is a $C_1$-$C_8$ alkylene group.

6. Compounds as claimed in claim 1 wherein R is a $C_1$-$C_8$ hydrocarbon chain group having arylene or ethylenic unsaturation interruption in its hydrocarbon chain.

7. A compound as claimed in claim 1 wherein R is a $C_2$ alkylene group.

8. A compound as claimed in claim 1 wherein R is a —$CH_2C(CH_2Br)_2$—$CH_2$— group.

9. A compound as claimed in claim 1 where R is —$CH_2C(Br)=C(Br)CH_2$—.

10. A compound as claimed in claim 4 where R is a $C_2$ alkylene group.

11. Compounds as claimed in claim 1 wherein R is —$CH_2$—$C_6H_4$—$CH_2$—.

* * * * *